US00PP31118P2

(12) United States Plant Patent
Wood

(10) Patent No.: US PP31,118 P2
(45) Date of Patent: Nov. 26, 2019

(54) ***ILEX* PLANT NAMED 'SMNIFA'**

(50) Latin Name: *Ilex x meserveae*
Varietal Denomination: SMNIFA

(71) Applicant: Timothy D. Wood, Spring Lake, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 16/350,430

(22) Filed: Nov. 15, 2018

(51) Int. Cl.
*A01H 5/00* (2018.01)

(52) U.S. Cl.
USPC ..... Plt./247

(58) Field of Classification Search
USPC ..... Plt./247
CPC ..... A01H 5/00
See application file for complete search history.

*Primary Examiner* — Annette H Para
(74) *Attorney, Agent, or Firm* — C. A. Whealy

(57) ABSTRACT

A new and distinct *Ilex* plant named 'SMNIFA', characterized by its uniform and mounding plant habit; freely branching habit; dense and bushy growth habit; dark green-colored leaves; and good garden performance and winter hardiness.

1 Drawing Sheet

Botanical designation: *Ilex* x *meserveae*.
Cultivar denomination: 'SMNIFA'.

BACKGROUND OF THE INVENTION

The present Invention relates to a new and distinct *Ilex* plant, botanically known as *Ilex* x *meserveae* and hereinafter referred to by the name 'SMNIFA'.

The new *Ilex* plant is a product of a planned breeding program conducted by the Inventor in Grand Haven, Mich. The objective of the breeding program was to develop new uniform *Ilex* plants that are unique in form and winter-hardy.

The new *Ilex* plant originated from an open-pollination in 2005 of *Ilex* x *meserveae* 'Winterglanz', not patented, as the female, or seed, parent with an unknown selection of *Ilex* x *meserveae*, as the male, or pollen, parent. The new *Ilex* plant was discovered and selected by the Inventor in 2011 as a single plant within the progeny of the stated open-pollination in a controlled environment in Grand Haven, Mich.

Asexual reproduction of the new *Ilex* plant by softwood cuttings in Grand Haven, Mich. since 2011 has shown that the unique features of the new *Ilex* plant are stable and reproduced true to type in successive generations of asexual reproduction.

SUMMARY OF THE INVENTION

Plants of the new *Ilex* have not been observed under all possible combinations of environmental conditions and cultural practices. The phenotype may vary somewhat with variations in environmental conditions such as temperature and light intensity without, however, any variance in genotype. The following traits have been repeatedly observed and are determined to be the unique characteristics of 'SMNIFA'. These characteristics in combination distinguish 'SMNIFA' as a new and distinct *Ilex* plant:

1. Uniform and mounding plant habit.
2. Freely branching habit; dense and bushy growth habit.

3. Dark green-colored leaves.
4. Good garden performance and winter hardiness.

Plants of the new *Ilex* differ primarily from plants of the female parent, 'Winterglanz', in plant habit as plants of the new *Ilex* are more compact and smaller than plants of 'Winterglanz'.

Plants of the new *Ilex* can be compared to the plants of *Ilex* x *meserveae* 'David Carroll', disclosed in U.S. Plant Pat. No. 26,926. In side-by-side comparisons, plants of the new *Ilex* differ from plants of 'David Carroll' in the following characteristics:

1. Plants of the new *Ilex* are more freely branching than plants of 'David Carroll'.
2. Plants of the new *Ilex* have dark green-colored leaves whereas plants of 'David Carroll' have bright yellow green-colored leaves.

BRIEF DESCRIPTION OF THE PHOTOGRAPH

The accompanying colored photograph illustrates the overall appearance of the new *Ilex* plant. The photograph show the colors as true as it is reasonably possible to obtain in colored reproductions of this type. Colors in the photograph may differ slightly from the color values cited in the detailed botanical description which accurately describe the colors of the new *Ilex* plant. The photograph is a side perspective view of a typical plant of 'SMNIFA' grown in a container.

DETAILED BOTANICAL DESCRIPTION

The aforementioned photographs and following observations and measurements describe plants grown during the spring and summer in five-gallon containers in a polyethylene-covered greenhouse in Grand Haven, Mich. and under cultural practices typical of commercial *Ilex* production. During the production of the plants, day temperatures ranged from 18° C. to 27° C. and night temperatures ranged from ranged from 5° C. to 10° C. Plants were three years old when the photograph and detailed description were taken. In the following description, color references are made to The Royal Horticultural Society Colour Chart, 2015 Edition, except where general terms of ordinary dictionary significance are used.

Botanical classification: *Ilex* x *meserveae* 'SMNIFA'.

Parentage:

*Female, or seed, parent.*—*Ilex* x *meserveae* 'Winterglanz', not patented.

*Male, or pollen, parent.*—Unknown selection of *Ilex* x *meserveae*, not patented.

Propagation:

*Type*.—By softwood cuttings.

*Time to initiate roots, winter*.—About 100 days at temperatures about 10° C. to 25° C.

*Time to produce a rooted young plant, summer*.—About one year at temperatures about 10° C. to 25° C.

*Root description*.—Medium in thickness; typically grey white in color, actual color of the roots is dependent on substrate composition, water quality, fertilizer, substrate temperature and physiological age of roots.

*Rooting habit*.—Moderately freely branching; medium density.

Plant description:

*Plant and growth habit*.—Perennial evergreen shrub; uniform and mounding plant habit; vigorous growth habit.

*Branching habit*.—Freely branching habit; dense and bushy growh habit with about 100 lateral branches developing per plant.

*Plant height*.—About 40 cm.

*Plant diameter, area of spread*.—About 52 cm.

*Lateral branch description*.—Length: About 24 cm. Diameter: About 7.5 mm. Internode length: About 1 cm. Strength: Strong. Aspect: Erect to about 45° from vertical. Texture: Smooth, glabrous; becoming woody with development. Color, developing: Close to 178A. Color, developed: Close to 138A.

*Leaf description*.—Arrangement: Alternate, simple. Length: About 4 cm. Width: About 2.5 cm. Shape: Elliptic. Apex: Acute. Base: Cuneate. Margin: Serrate with spines. Venation pattern: Pinnate. Texture and luster, upper and lower surfaces: Smooth, glabrous; glossy. Color: Developing leaves, upper surface: Close to 146B. Developing leaves, lower surface: Close to 146D. Fully expanded leaves, upper surface: Close to N189A; venation, close to 144C. Fully expanded leaves, lower surface: Close to 146B; venation, close to 146B. Petioles: Length: About 5 mm. Diameter: About 2 mm. Texture, upper and lower surfaces: Smooth, glabrous. Color, upper surface: Close to 176A. Color, lower surface: Close to 199D.

Flower description:

*Flower appearance and arrangement*.—Single axillary rotate flowers arranged in clusters of two to five flowers; flowers face upright to outwardly.

*Natural flowering season*.—Plants flower in early spring in Michigan; flowers not persistent.

*Fragrance*.—None detected.

*Flower diameter*.—About 4 mm.

*Flower length (height)*.—About 9 mm.

*Flower buds*.—Length: About 3 mm. Diameter: About 2 mm. Shape: Spherical to oblong. Color: Close to 157B.

*Petals*.—Quantity and arrangement: About four in a single whorl. Length: About 4 mm. Width: About 3 mm. Shape: Oblong. Apex: Obtuse, cupped upwardly. Base: Truncate. Margin: Entire. Texture, upper and lower surfaces: Smooth, glabrous. Color: When opening, upper surface: Close to 155C; distal spot, close to 4C. When opening, lower surface: Close to 155C. Fully opened, upper and lower surfaces: Close to 155C; color does not change with development.

*Sepals*.—Quantity and arrangement: About four in a single whorl. Length: About 1 mm. Diameter: About 1 mm. Shape: Obovate. Apex: Acute. Base: Truncate. Margin: Entire. Texture, upper and lower surfaces: Smooth, glabrous. Color, upper and lower surfaces: Close to 145B.

*Peduncles*.—Length: About 4 mm. Diameter: About 1 mm. Aspect: Upright to outwardly. Strength: Moderately strong. Texture: Smooth, glabrous. Color: Close to 145B.

*Reproductive organs*.—Androecium: Quantity per flower: About four. Filament length: Less than 1 mm. Filament color: Close to 155C. Anther length: Less than 1 mm. Anther shape: Elliptic. Anther color: Close to 155C. Pollen amount: Scarce. Pollen color: Close to 155C. Gynoecium: Quantity per flower: One. Pistil length: About 3 mm. Style length: About 3 mm. Style color: Close to 144B. Stigma shape: Globular. Stigma color: Close to 151A. Ovary color: Close to 151C.

*Fruits*.—Length: About 8 mm. Diameter: About 8 mm. Shape: Spherical. Texture: Smooth, glabrous. Color, developing: Close to 150A. Color, developed: Close to 45B.

Garden performance: Plants of the new *Ilex* have been observed to have good garden performance and to be tolerant to rain, wind and temperatures ranging from about −32° C. to about 36° C.

Pathogen & pest resistance: Plants have not been observed to be resistant to pathogens and pests common to *Ilex* plants.

It is claimed:

1. A new and distinct *Ilex* plant named 'SMNIFA' as illustrated and described.

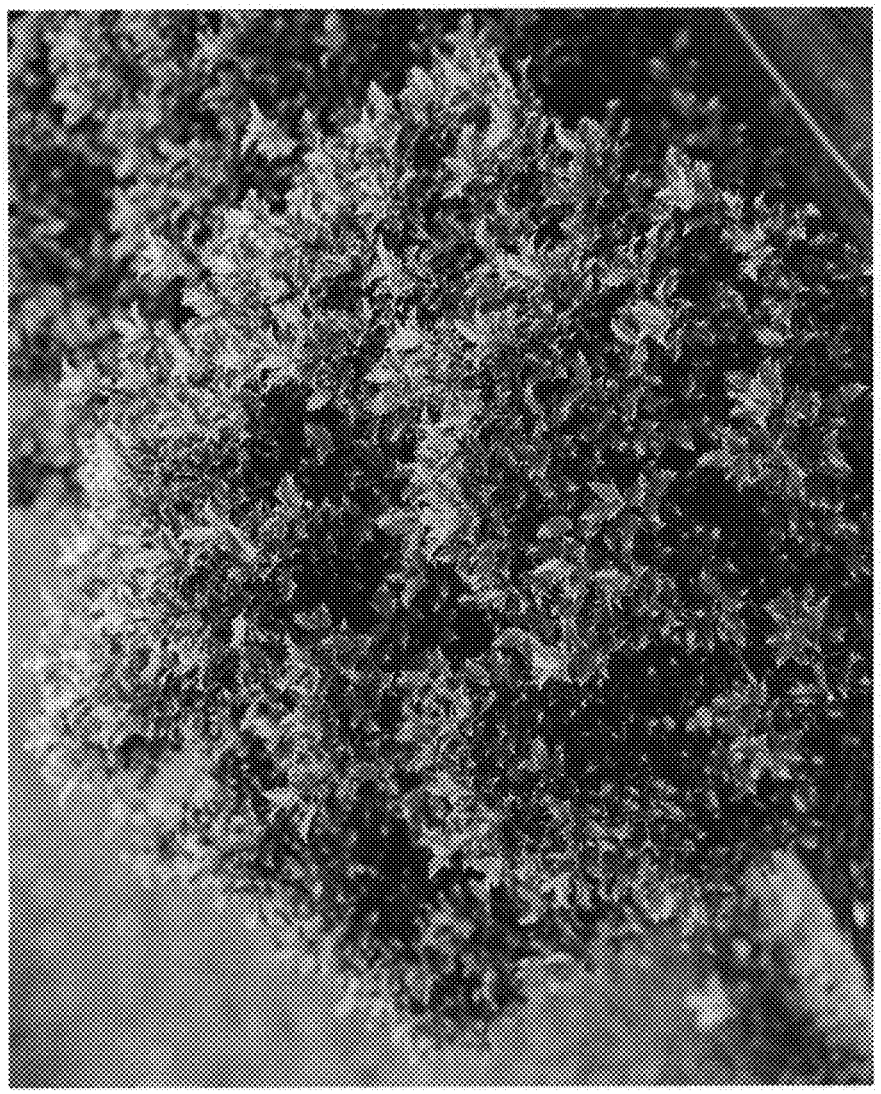

* * * * *